United States Patent

Routh et al.

[11] Patent Number: 5,843,133
[45] Date of Patent: Dec. 1, 1998

[54] DYNAMIC BANDWIDTH CONTROL IN AN IMPLANTABLE MEDICAL CARDIAC STIMULATOR

[75] Inventors: Andre Routh, Lake Jackson, Tex.; Annette Bruls, Brussels, Belgium; Drury Woodson, III, Alvin; Joseph Vandegriff, Brazoria, both of Tex.; Yves Verboven, Kessel-lo, Belgium

[73] Assignee: Sulzer Intermedics Inc., Angleton, Tex.

[21] Appl. No.: 843,236

[22] Filed: Apr. 14, 1997

[51] Int. Cl.[6] .................................................. A61N 1/18
[52] U.S. Cl. ............................ 607/14; 600/518; 607/30
[58] Field of Search .................................. 607/27, 9, 14, 607/28, 30, 32; 600/515, 518

[56] References Cited

U.S. PATENT DOCUMENTS

| | | | |
|---|---|---|---|
| 4,527,568 | 7/1985 | Rickards | 128/419 |
| 4,663,701 | 5/1987 | Stotts | 363/60 |
| 4,726,379 | 2/1988 | Altman et al. | 607/9 |
| 4,856,523 | 8/1989 | Sholder et al. | 128/419 |
| 4,903,699 | 2/1990 | Baker, Jr. et al. | 128/419 |
| 4,913,145 | 4/1990 | Stotts | 128/419 |
| 5,052,388 | 10/1991 | Sivula et al. | 128/419 |
| 5,103,819 | 4/1992 | Baker et al. | 128/419 |
| 5,190,052 | 3/1993 | Schroeppel | 128/786 |
| 5,205,283 | 4/1993 | Olson | 600/518 |
| 5,350,409 | 9/1994 | Stoop et al. | 67/17 |
| 5,391,189 | 2/1995 | van Krieken et al. | 607/17 |
| 5,431,693 | 7/1995 | Schroeppel | 607/28 |
| 5,443,485 | 8/1995 | Housworth et al. | 607/28 |
| 5,543,795 | 8/1996 | Fernald | 341/163 |
| 5,571,144 | 11/1996 | Schroeppel | 607/28 |
| 5,573,550 | 11/1996 | Zadeh et al. | 607/28 |
| 5,685,315 | 11/1997 | McClure et al. | 607/4 |

OTHER PUBLICATIONS

Larry J. Stotts; Introduction to Implantable Biomedical IC Design; Jan., 1989; pp. 12–19; IEEE Circuits and Devices Magazine.

Primary Examiner—William E. Kamm
Assistant Examiner—Kennedy J. Schaetzle
Attorney, Agent, or Firm—John R. Merkling; Conley, Rose & Tayon

[57] ABSTRACT

An implantable medical device for electrically stimulating the heart to beat includes a sense circuit for detecting cardiac electrical activity. The sense circuit includes a band pass filter with an adjustable frequency response. The frequency response can be repeatedly adjusted after implantation of the medical device and preferably is adjusted upon detection of the loss of normal sinus rhythm (NSR) in the heart's atria. The loss of NSR often indicates atrial fibrillation (AF), and the filter's frequency response is adjusted to increase the sensitivity of the sense circuit to the cardiac electrical activity typical during AF. The medical device is calibrated during implantation or at subsequent doctor visits with the aid of a calibration device external to the body. Cardiac electrical activity in the form of an electrogram is transmitted from the medical device to the external calibration device. The transmitted electrogram preferably includes both NSR and AF rhythms. The calibration device computes two sets of filter coefficients; one set for increased filter sensitivity during NSR and another set for increased sensitivity during AF. The coefficients are transmitted to the medical device which uses the appropriate set of coefficients to increase the filter's frequency response during both NSR and AF.

24 Claims, 7 Drawing Sheets

DYNAMIC BANDWIDTH CONTROL IN AN IMPLANTABLE MEDICAL CARDIAC STIMULATOR

BACKGROUND OF THE INVENTION

1. Field of the Invention

The present invention relates generally to cardiac stimulating devices, such as pacemakers and defibrillators. More particularly, the present invention relates to a cardiac stimulating device that is capable of operating in multiple modes of operation. Still more particularly, the present invention relates to a cardiac stimulating system that enhances detection of atrial rhythms.

2. Description of the Related Art

In the normal human heart, illustrated in FIG. 1, the sinus (or sinoatrial (SA)) node generally located near the junction of the superior vena cava and the right atrium constitutes the primary natural pacemaker by which rhythmic electrical excitation is developed. The cardiac impulse arising from the sinus node is transmitted to the two atrial chambers (or atria) at the right and left sides of the heart. In response to excitation from the SA node, the atria contract, pumping blood from those chambers into the respective ventricular chambers (or ventricles). The impulse is transmitted to the ventricles through the atrioventricular (AV) node, and via a conduction system comprising the bundle of His, or common bundle, the right and left bundle branches, and the Purkinje fibers. The transmitted impulse causes the ventricles to contract, the right ventricle pumping unoxygenated blood through the pulmonary artery to the lungs, and the left ventricle pumping oxygenated (arterial) blood through the aorta and the lesser arteries to the body. The right atrium receives the unoxygenated (venous) blood. The blood oxygenated by the lungs is carried via the pulmonary veins to the left atrium.

This action is repeated in a rhythmic cardiac cycle in which the atrial and ventricular chambers alternately contract and pump, then relax and fill. Four one-way valves, between the atrial and ventricular chambers in the right and left sides of the heart (the tricuspid valve and the mitral valve, respectively), and at the exits of the right and left ventricles (the pulmonic and aortic valves, respectively, not shown) prevent backflow of the blood as it moves through the heart and the circulatory system.

Disruption of the natural pacemaking and propagation system as a result of aging or disease is commonly treated by artificial cardiac pacing, by which rhythmic electrical discharges are applied to the heart at a desired rate from an artificial pacemaker. An artificial pacemaker (or "pacer" as it is commonly labeled) is a medical device which delivers electrical pulses to an electrode that is implanted adjacent to or in the patient's heart in order to stimulate the heart so that it will contract and beat at a desired rate. If the body's natural pacemaker performs correctly, blood is oxygenated in the lungs and efficiently pumped by the heart to the body's oxygen-demanding tissues. However, when the body's natural pacemaker malfunctions, an implantable pacemaker often is required to properly stimulate the heart. An in-depth explanation of certain cardiac physiology and pacemaker theory of operation is provided in U.S. Pat. No. 4,830,006.

Pacers today are typically designed to operate using one of three different response methodologies, namely, asynchronous (fixed rate), inhibited (stimulus generated in the absence of a specified cardiac activity), or triggered (stimulus delivered in response to a specified hemodynamic parameter). Broadly speaking, the inhibited and triggered pacemakers may be grouped as "demand" type pacemakers, in which a pacing pulse is only generated when demanded by the heart. To determine when pacing is required by the pacemaker, demand pacemakers may sense various conditions such as heart rate, physical exertion, temperature, and the like. Moreover, pacemaker implementations range from the simple fixed rate, single chamber device that provides pacing with no sensing function, to highly complex models that provide fully automatic dual chamber pacing and sensing functions. The latter type of pacemaker is the latest in a progression toward physiologic pacing, that is, the mode of artificial pacing that most closely simulates natural pacing.

Because of the large number of options available for pacer operation, an industry convention has been established whereby specific pacer configurations are identified according to a code comprising three, four or five letters. The fifth code position describes the antitachycardia functions, if any. Because this position is not applicable to most commonly used pacemaker types, most common codes comprise either three or four letters are shown in the table below. For this reason and for simplicity's sake, the fifth code position is omitted from the following table. Each code can be interpreted as follows:

| Code position | 1 | 2 | 3 | 4 |
|---|---|---|---|---|
| Function identified | chamber paced | chamber sensed | response to sensing | programmability, rate modulation |
| Options available | 0 - none | 0 - none | 0 - none | 0 - none |
| | A - atrium | A - atrium | T - triggered | P - programmable |
| | V - ventricle | V - ventricle | I - inhibited | M - multiprogrammable |
| | D - dual | D - dual | D - dual | C - communicating |
| | (A + V) | (A + V) | (T + I) | R - rate modulating |

The sinus node is spontaneously rhythmic, and the cardiac rhythm it generates is termed normal sinus rhythm ("NSR") or simply sinus rhythm. This capacity to produce spontaneous cardiac impulses is called rhythmicity, or automaticity. Some other cardiac tissues possess rhythmicity and hence constitute secondary natural pacemakers, but the sinus node is the primary natural pacemaker because it spontaneously generates electrical pulses at a faster rate. The secondary pacemakers tend to be inhibited by the more rapid rate at which impulses are generated by the sinus node.

For example, a DDD pacer paces either chamber (atrium or ventricle) and senses in either chamber. Thus, a pacer in DDD mode, may pace the ventricle in response to electrical activity sensed in the atrium. A VVI pacer paces and senses in the ventricle, but its pacing is inhibited by spontaneous electrical activation of the ventricle (i.e., the ventricle paces itself naturally). In VVIR mode, ventricular pacing is similarly inhibited upon determining that the ventricle is naturally contracting. With the WIR mode, the pacer's pacing rate, however, in the absence of naturally occurring pacing, is modulated by the physical activity level of the patient.

Pacers commonly include accelerometers to provide an indication of the patient's level of physical activity.

Of the many possible pacer configurations, only four or five are commonly used today. These common configurations or modes are VVI, VVIR, AAIR, VDD, DVI, DDD and DDDR. Most pacers are capable of switching between two or more of these various operational modes depending on the condition of the patient.

An exemplary rhythm of the electrical activity in the left or right atrium is shown in FIG. 2. A rhythm representing atrial electrical activity is termed an "atrial electrogram" or "AEGM". An AEGM typically is measured by implanting a pair of electrodes in the right atrium and amplifying the signal received by the electrodes. A threshold detector commonly used in pacers identifies events in the AEGM by comparing the AEGM signal amplitude to a predetermined threshold level. When the AEGM signal exceeds the threshold level, an event is registered by the pacer. The AEGM in FIG. 2 shows atrial electrical excitation during normal sinus rhythm in the left-hand side of the waveform. The electrical impulse generated by the SA node to initiate atrial contraction is detected by the atrial electrodes at events 50. Events 50 are commonly called "A waves" or "atrial senses" (AS).

Abnormal rhythms are termed arrhythmias. Tachyarrythmias are abnormally fast rhythms. One common type of atrial tachyarrhythmia is referred to as atrial fibrillation (AF). During AF, the atria do not contract, but move very little, merely quivering. An episode of AF is shown in the right-hand side of FIG. 2. As shown the normal atrial electrogram collapses and fractionates becoming noisy. While normal sinus rhythm (NSR) includes a consistent AEGM signal, atrial fibrillation, in contrast, is described as being "irregularly irregular." Occasionally, atrial electrical activity during AF, such as at events 52, 53, may exceed the threshold level of the threshold detector and therefore be registered as an A wave by the pacer. A conventional pacer, therefore, may misinterpret these events as naturally occurring contractions of the atria. Events 52, 53, do not represent atrial contractions, however, but merely represent a random buildup of electrical activity in the atrium near the atrial electrode, characteristic of atrial fibrillation.

Detection of a rapid succession of events 53 provides an indication of atrial fibrillation. However, because of the irregular nature of the AEGM during AF, a conventional pacer may sporadically detect AF. Accurate and continuous detection of AF is frustrated further by myopotentials (i.e., electrical signals from muscle tissue) which cause noise to be superimposed on the electrogram signal. Myopotential noise generated by the pectoral muscles, for example, near which pacemakers electrodes are typically implanted, may be particularly disruptive to the normal operation of a pacemaker and even inhibit pacing when the pacer is unable to distinguish myopotential noise from AEGM signals. Accurate detection of AF is critical to prevent the pacer from inappropriately switching between operational modes, as explained below.

Many pacemakers operate in the DDD mode of operation during normal sinus rhythm as indicated in FIG. 2. In this mode, electrical excitations in the atrium are detected as atrial senses 50. Upon detection of an atrial sense, a DDD pacer waits a brief period of time T (commonly called the atrio ventricular delay) to allow the ventricles an opportunity to fill with blood and then paces the ventricle by providing a ventricular pacing pulse (VP) through the ventricular electrodes causing the ventricle to contract. The first three events 50 in the AEGM of FIG. 2 follow this methodology.

At the onset of atrial fibrillation, the benefit of a DDD pacer (ventricular pacing following detection of A waves) to pump blood is diminished because the sensed atrial events do not represent actual atrial contractions, and because they occur at such a rapid rate that ventricular pacing in response to the rapid atrial detections is inefficient given that the ventricles do not have time to fill in the time between pacing pulses. Rapid ventricular pacing without affording the ventricles time to fill causes the patient to become breathless and lightheaded. A DDD pacer thus switches to an alternative mode such as VVIR mode when atrial fibrillation is detected. The mode switch may occur, for example, at point 55 in FIG. 2 when the pacer detects a series of atrial senses 53 in rapid succession. As explained above, a VVIR pacer paces the ventricles in response to an activity sensor which provides an estimate of metabolic demand which can be used to determine an appropriate pacing rate. The ventricular pace pulses during the VVIR mode of operation thus are disassociated from any detected atrial sense activity; that is, VP pulses are generated by the pacer at a rate determined only by the metabolic demand of the patient as estimated by the pacer's activity sensor. Once the AF ceases and NSR begins again, the pacer mode switches back to DDD mode. A pacer that detects AF sporadically throughout a continuous episode of AF will mode switch repeatedly between modes, such as DDD and VVIR modes.

Thus, although VVIR pacers normally ignore electrical activity detected by the atrial electrodes, for a variety of reasons it is important to be able to detect and monitor accurately electrical excitation in the atrium upon switching to VVIR mode. Because of the difficulty in accurately detecting AF, a pacer may unnecessarily switch between modes, such as DDD and VVIR, repeatedly over a short period of time if AF is not detected accurately. Each time the pacer mode switches, the pacing rate may change dramatically resulting from the different criteria that are used to determine the pacing rate in the various modes. Sudden rises or drops in pacing rate may be harmful to the patient causing tiredness, faintness nausea, and palpitations. Thus, while it is incumbent for a pacer to switch modes as necessary for the patient's health, mode switching must be carefully controlled to prevent repeated unnecessary mode switches. Careful and accurate monitoring of the atrial electrogram allows a pacer to switch modes appropriately.

Although various criteria have been used to detect the onset of atrial fibrillation such as high average detection rate, irregular detection of atrial fibrillation and constantly changing signal morphology (amplitude and polarity), many problems exist making detection and accurate monitoring of atrial fibrillation difficult as discussed above. These problems have not been fully resolved by present day pacing systems. Thus, it would be desirable to provide a pacer that can switch modes of operation once normal sinus rhythm ceases, which, for example, may occur upon the initiation of atrial fibrillation. It would be further desirable to provide a pacer with an enhanced ability to detect accurately and monitor an atrial electrogram signal during periods of atrial fibrillation and to distinguish AF from other arrythmias.

SUMMARY OF THE INVENTION

Accordingly, there is herein provided an implantable medical device such as a pacemaker for electrically stimulating the heart to beat. The implantable medical device includes an atrial sense circuit for detecting and monitoring electrical activity in the atria of the heart, such activity commonly known as the atrial electrogram. The sense circuit includes a band pass filter to increase the medical device's sensitivity to the differing electrograms that are generated during normal sinus rhythm (NSR) and atrial tachyarrythmia. During atrial tacharrythmias such as atrial fibrillation (AF), atrial flutter, and the like, the character of the atrial electrogram changes dramatically from its NSR characteristics, usually with a shift in the electrogram's frequency spectrum to a frequency range different than for NSR, and with a change in signal amplitude. Accordingly, the band pass filter in the atrial sense circuit is dynamically adjustable to provide increased sensitivity to varying atrial electrogram conditions. The frequency response of the atrial filter can be repeatedly adjusted after implantation of the medical device. Upon detection of the loss of NSR in the heart's atria, the frequency response preferably is adjusted to a response that provides increased sensitivity to AF. Likewise, upon return of NSR, the frequency response is adjusted back to a response that provides increased sensitivity to NSR.

The character of the atrial electrogram during NSR and during AF varies from patient to patient and thus the present invention is tailored for each patient in which the pacemaker is implanted. The medical device is adjusted during implantation or later with the aid of an external programmer external to the body. Cardiac electrical activity in the form of an electrogram is transmitted from the medical device to the external programmer. The transmitted electrogram preferably includes both NSR and AF rhythms. The programmer computes two sets of filter coefficients which define the frequency responses of the dynamically adjustable band pass filter. One set provides increased filter sensitivity during NSR and the other set provides increased sensitivity during AF. The two sets of coefficients then are transmitted to the medical device and used during normal pacer operation.

During normal operation, the medical device uses the coefficients determined during the tailoring operation to set the filter's frequency response during NSR and AF. During NSR, the frequency response of the filter is set to provide increased sensitivity to NSR. Upon detection of AF, the filter's frequency response is changed to increase sensitivity to AF.

BRIEF DESCRIPTION OF THE DRAWINGS

Other objects and advantages of the invention will become apparent upon reading the following detailed description and upon reference to the accompany drawings, wherein.

DETAILED DESCRIPTION OF THE INVENTION

Figure 3:
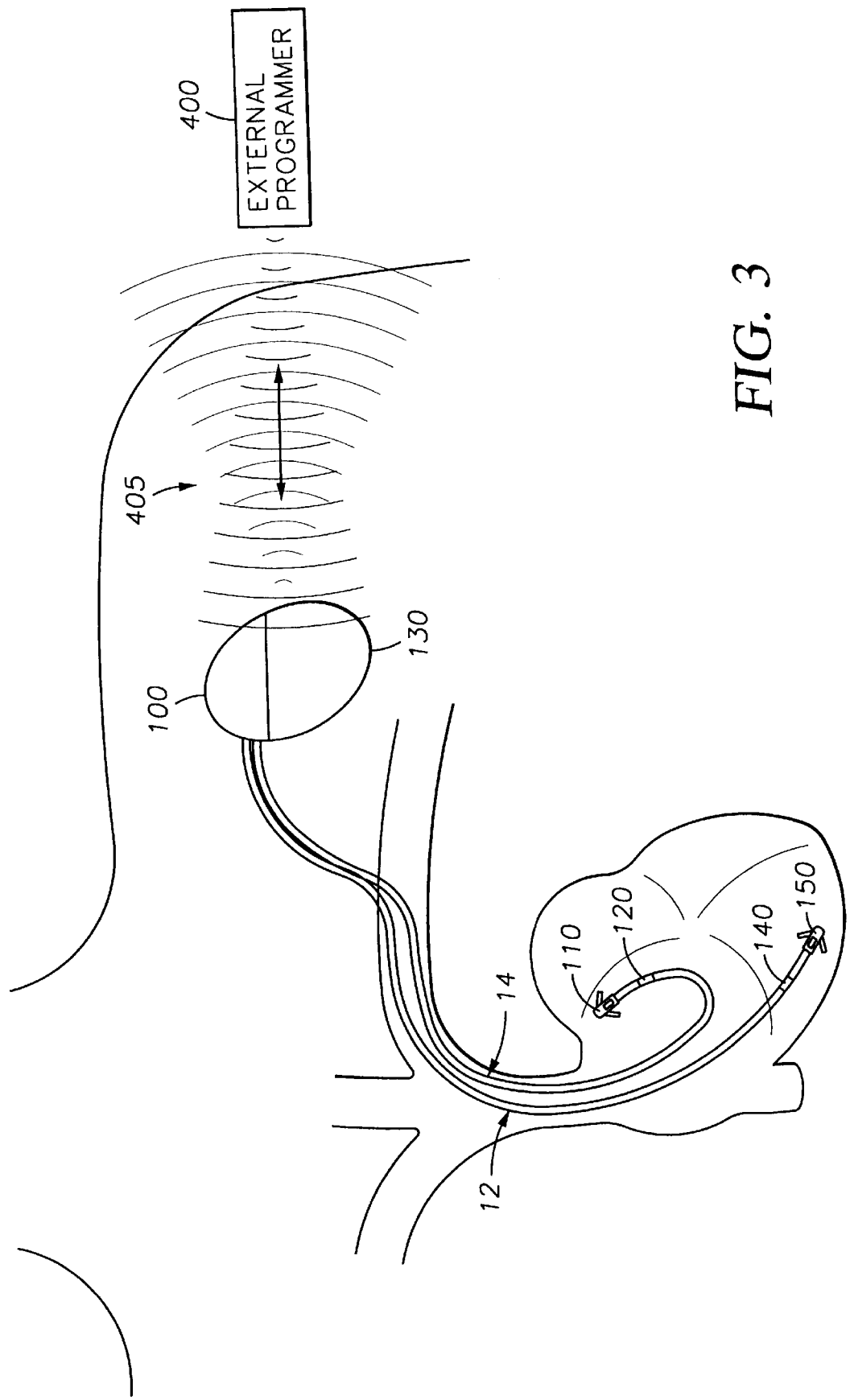
FIG. 3 is a schematic diagram of a pacer constructed in accordance with the present invention implanted in a human body.

Referring now to FIG. 3, an implantable medical device 100 constructed in accordance with the preferred embodiment is shown implanted and coupled to the patient's heart by leads 12, 14. Medical device 100 communicates with an external programmer 400, described below. The communication path is shown by reference numeral 405. The implantable medical device 100 may include a pacemaker or any medical device that performs pacing functions. For purposes of describing the preferred embodiments of the invention, the implantable medical device will hereafter be described as an implantable pacemaker or simply pacer 100. However, it should be understood that the invention may likewise be employed in any of a variety of implantable medical devices, such as defibrillators.

In the dual chamber pacing arrangement shown, leads 12, 14 are positioned in the right ventricle and right atrium, respectively. Alternatively leads may be connected to the left ventricle and left atrium. Each lead 12, 14 includes at least one stimulating electrode for delivery of electrical impulses to excitable myocardial tissue in the appropriate chamber(s) in the right side of the patient's heart. As shown in FIG. 3, each lead 12, 14 includes two electrodes. More specifically, lead 14 includes tip electrode 110 and ring electrode 120, and lead 12 includes tip electrode 150 and ring electrode. As one skilled in the art will understand, two, three, and four terminal devices all have been used or suggested as possible electrode schemes and may be employed in the present invention.

Figure 4:
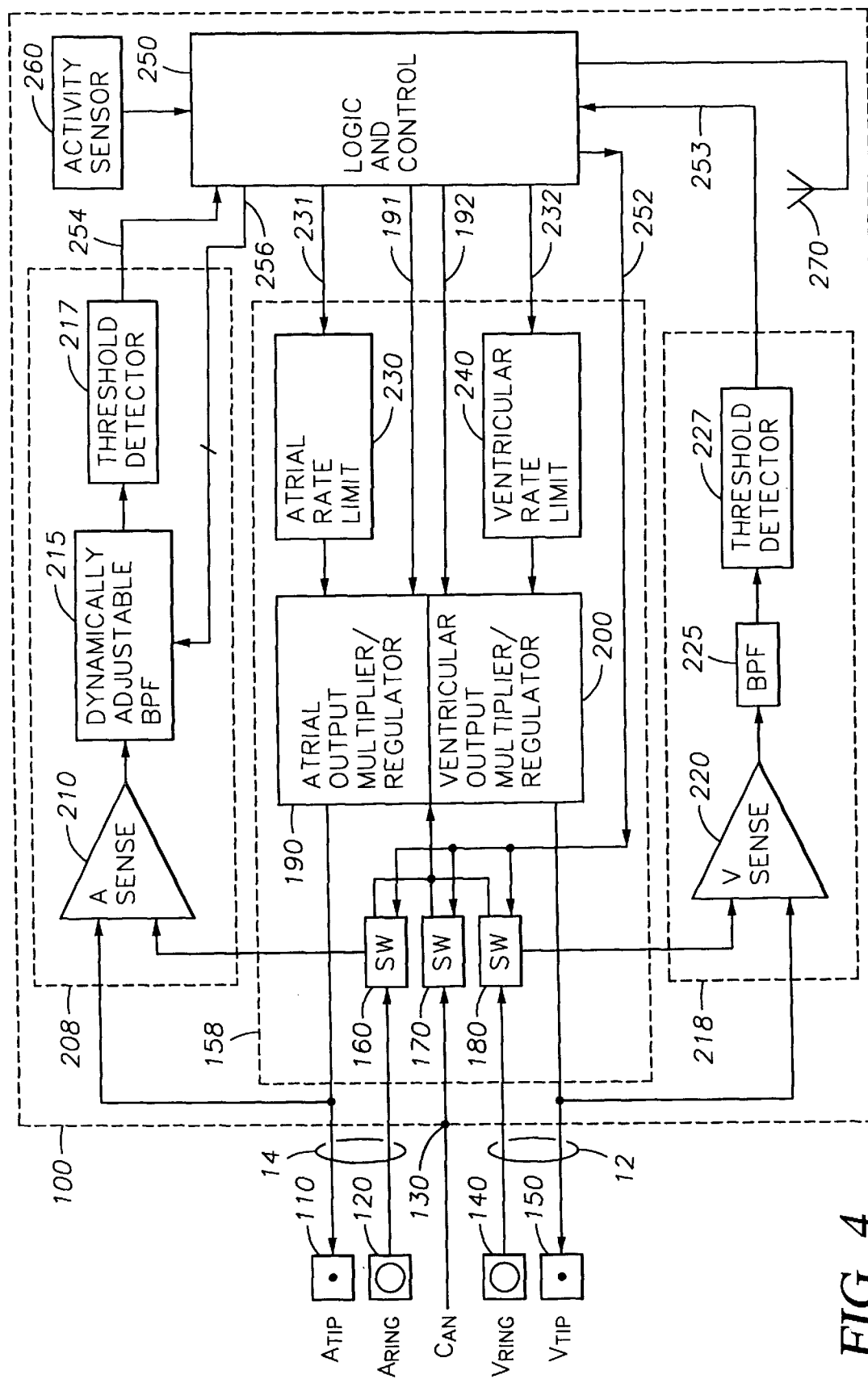
FIG. 4 is a block diagram of the pacer of FIG. 3 showing a dynamically adjustable band pass filter for use in adjusting the sensitivity for atrial detection.

Pacer 100 includes housing or can 130 that houses a conventional battery (not shown), pacing circuit 158, atrial sense circuit 208, ventricular sense circuit 218, logic and control unit 250, activity sensor 260, and telemetry unit 270, best shown in FIG. 4. Can 130 preferably is made of titanium, or another biocompatible metal.

Referring to FIG. 4, pacing circuit 158 delivers the appropriate atrial or ventricular pacing pulses as initiated by logic and control unit 250 to the heart generally through one or more electrodes 110, 120, 140, 150 or can 130. Electrodes 110, 120, 140, 150, can 130 are also employed for sensing atrial and ventricular contractions, as explained below.

Atrial sense circuit 208 provides an indication on line 254 to logic and control unit 250 when the atrium contracts. Similarly, ventricular sense circuit 218 indicates to logic and control unit 250 on line 253 when the ventricles contract. Activity sensor 260 preferably includes an accelerometer and provides a signal to logic and control unit 250 from which the level of activity of the patient can be determined, according to known principles. This signal is used to estimate metabolic demand. Other types of activity sensors such as piezoelectric crystals and pressure sensors can also be used. Further, it is possible to determine activity level without a dedicated activity sensor through the use of known techniques such as Q-T interval and estimating minute ventilation from electrical impedance. Thus, the invention may use an activity sensor or may alternatively determine activity level through other means.

Telemetry unit 270 allows two-way communication between pacer 100 and a device external to the body such as external programmer 400 (FIG. 3). Communication may be in accordance with any one of a variety of known techniques such as transcutaneous energy transmission which employs a pair of coils of conductors, one located external to the body and the other implanted. An example of transcutaneous energy transmission is disclosed in U.S. Pat. No. 5,411,537, which is incorporated herein by reference. Telemetry unit 270 may be located within can 130 are shown in FIGS. 3 and 4, or may be separately implanted outside the can and coupled to pacer 100 through electrical conductors.

Logic and control unit 250 generally controls the operation of pacer 100 and determines when to stimulate the atria and ventricles to contract. Pacer 100 preferably also includes a memory device such as random access memory (RAM) for storing a variety of information such as heart rate data and other physiological information, status and configuration information pertaining to the operation of the pacer, and the like. Such RAM preferably is provided in the logic and control unit 250 and thus is not specifically shown. A suitable control unit 250 includes a microprocessor controller such as the 8051 controller by Intel.

Pacing energy is delivered to the heart through the electrodes in a variety of modes or configurations using logic and control unit 250 and pacing circuit 158. Pacing circuit 158 preferably includes switches 160, 170, 180, atrial and ventricular output multiplier/regulators 190, 200, and atrial and ventricular rate limiters 230, 240. Logic and control unit 250 provides pacing pulses to the rate limiters 230, 240 via lines 231, 232, respectively, and controls the state of switches 160, 170, 180 via lines 252. Although logic and control unit 250 determines when to pace the atria and/or ventricles, rate limiters 230, 240 ensure that the cardiac chambers are not paced at a rate in excess of an upper limit encoded into the rate limiters. The rate limiters, therefore, provide extra protection against pacing the heart at an excessively high rate.

A signal substantially equivalent to the voltage of the pacer's battery (not shown), which is between approximately 2 and 3 volts (preferably 2.8 volts), is delivered to one of the output multiplier/regulators 190, 200 corresponding to the chamber to be paced as determined by logic control unit 250. Thus, if it is desired to pace the atria, logic and control unit 250 delivers a pulse to atrial output multiplier/regulator 190, the pulse rate limited by atrial rate limiter 230. Similarly, to pace the ventricle, logic and control unit 250 delivers a pacing pulse to ventricular output multiplier/regulator 200 is limited by ventricular limiter 240. Output multiplier/regulators 190, 200 preferably increase or decrease the magnitude of the voltage received from the logic and control unit 250. Output multiplier/regulators 190, 200 convert the pulse received from logic and control unit 250 through the rate limiters 230, 240 to a voltage level sufficient to cause the chambers to contract, commonly called "capture". The magnitude of the voltage output by the output multiplier/regulators 190, 200 necessary for proper pacing depends on various factors known to those of ordinary skill in the art such as which chamber is being paced, electrode placement within the chamber, and the physiology of the patient's heart. Output multiplier/regulator/regulators 190, 200 also control the width or duration of the pulse delivered to the heart. The width of the output pulses to the heart are specified by the logic and control unit 250 over control lines 191,192.

Output multiplier/regulators 190, 200 provide pacing pulses to the heart through electrodes 110,120, 140, 150 and can 130 and via switches 160, 170, 180. The electrodes shown schematically in FIG. 4 include two atrial electrodes (Atip 110 and Aring 120), two ventricular electrodes (Vtip 140 and Vring 150), and can 130. Can 130 represents the conducting enclosure housing the pacer's electronics as previously described. When coupled to a signal reference in the pacer, such as the positive terminal of the battery (not shown), the can is usable as a fifth electrode, as those of ordinary skill in the art will understand. Although pacer 100 is thus shown with five electrodes, any number of electrodes is consistent with the preferred embodiment.

Switches 160,170,180 are interposed between electrodes 120,140 and can 130, output multiplier/regulators 190, 200, and sense amplifiers 220 of ventricular sense circuit 218. Switches 160, 170, 180, which are preferably conventional solid state switches provide the capability to support either unipolar or bipolar pacing. Pacer 100 may pace the heart in a unipolar mode in which pacing energy is delivered through either tip electrode 110 or 150 and returned through can 130. To implement unipolor mode, logic and control unit 250 opens switches 160, 180 and closes switch 170. As used herein, an "open" switch state prevents current from flowing through the switch and a "closed" switch state allows current to flow through the switch. With switch 170 closed, and switches 160, 180 open, any pacing current delivered through either tip electrode 110, 150 returns to the can 130 and not through the ring electrodes 120, 140. Thus, unipolar pacing of the atrium is achieved by delivering a pacing pulse through the Atip electrode 110 with the return current path through can 130. Similarly, the ventricle can be paced in a unipolar configuration by delivering a pacing pulse through the Vtip electrode 150 with the current path through can 130.

In a bipolar mode, a pacing pulse preferably is delivered through one of the atrial or ventricular tip electrodes 110, 150 with a return current path through one of the ring electrodes 120, 140 depending on the state of switches 160, 180. During bipolar pacing, switch 170 remains open precluding a return current path through can 130. Bipolar atrial pacing can be implemented by opening switch 160 and closing switches 170, 180. In this mode, a pacing pulse delivered to the heart through Atip electrode 110 returns through the Aring electrode 120 and switch 160. Similarly, bipolar ventricular pacing can be implemented by opening switch 180 and closing switches 160, 170 allowing a pacing pulse to be delivered to the heart through Vtip electrode 150 returns through the Vring electrode 140 and switch 180.

Pacer 100 preferably is a demand-type pacemaker and paces the heart in response to one or more physiological signals or parameters such as heart rate and activity level. To enhance detection of atrial and ventricular electrical activity, pacer 100 includes atrial and ventricular sense circuits 208, 218, respectively. Ventricular sense circuit 218 includes a sense amplifier 220, band pass filter 225, and threshold detector 227. Sense amplifier 220 amplifies the voltage across the ventricular pair of electrodes 140, 150. Sense amplifier 220 is a low power amplifier preferably operating from a power supply of approximately one microamp of current. A suitable sense amplifier is disclosed in U.S. Pat. No. 4,913,145, and incorporated herein by reference.

Any periodic signal (i.e., a waveform that repeats itself at a constant rate) can be represented as a sum of an infinite number of sine waves of varying amplitude and frequency. The frequency of a periodic signal, such as a sine wave, represents the number of cycles of the waveform per second and typically is measured in units of cycles per second or Hertz (Hz). Electrical filters are circuits that amplify or pass signals within a certain frequency range and attenuate signals at all other frequencies. Thus, filters can separate a periodic signal into its constituent frequency components. Common filters include low pass filters (which pass low frequency signals and attenuate higher frequency signals), high pass signals (which pass high frequency signals and attenuate lower frequency signals), and band pass filters (which pass signals within a band of frequencies and attenuate signals at both lower and higher frequencies, i.e., signals outside the band). The band of frequencies that are passed by a band pass filter is commonly called the "pass band" and all frequencies outside the pass band lie in the "stop band"of the filter.

Referring still to FIG. 4, to enhance the signal from ventricular sense amplifier 220, ventricular sense circuit 218 includes a band pass filter 225. Band pass filter 225 preferably is a switched capacitor filter such as that disclosed in U.S. Pat. No. 4,913,145, or any other suitable low power, reliable filter suitable for use in implantable pacemakers. The transition in the frequency response of band pass filter 225 between the pass band and stop band may be gradual or sharp, depending on the number of poles included in the filter's design. The poles are the roots of the denominator polynomial of the filter's transfer function and are known by those of ordinary skill in the art. Band pass filter 225 preferably includes eight poles, although more or fewer poles are permissible.

Threshold detector 227 compares the signal provided to it by band pass filter 225 to a reference signal (not specifically shown) and provides an output signal to logic and control unit 250 on line 253. The output signal on line 253 generally indicates when the band pass filter's output signal exceeds the reference signal. The reference signal may be fixed or programmable by logic and control unit 250. The reference signal preferably is indicative of the minimum voltage level indicative of ventricular contraction. Thus, when the magnitude of the output signal of band pass filter 225 exceeds the magnitude of the reference signal, the ventricle likely is contracting. The output signal from threshold detector 227 may be encoded as a binary signal; that is, a logic high signal may indicate when the band pass filter's output exceeds the reference signal, and a logic low signal may indicate when the filter's output signal is below the reference signal.

Although the ventricular sense amplifier 220, band pass filter 225, and threshold detector 227 are shown as three separate components in the block diagram of FIG. 4, one of ordinary skill will recognize that these components may be combined into a single circuit or circuits, and this is typically the case for implantable pacemakers. For example, band pass filter 225 may be implemented using known switched capacitor technology that includes amplification for signals in the pass band of the filter. Also, ventricular sense amplifier 220, band pass filter 225, and threshold detector 227 may be provided in a different order than that shown. The arrangement of ventricular sense amplifier 220 and band pass filter 227, for example, may be reversed with band pass filter 225 coupled to the ventricular electrodes directly and then followed by ventricular sense amplifier 220.

Referring still to FIG. 4, atrial sense circuit 208 detects atrial electrical activity and comprises atrial sense amplifier 210 coupled to dynamically adjustable band pass filter (DABPF) 215 which couples to threshold detector 217. DABPF 215 preferably is a switched capacitor filter of similar construction to ventricular band pass filter 225, although other types of filters may be employed in the present invention. As with the ventricular sense circuit, atrial sense amplifier 210, DABPF 215, and threshold detector 217 may be combined into a single circuit or circuits or may be provided in an order other than that shown in FIG. 4. Atrial sense amplifier 210 and threshold detector 217 are of similar construction to ventricular sense amplifier 220 and threshold detector 227, which are discussed above. It should be recognized, however, that the gain of atrial sense amplifier 210 and the magnitude of the reference signal in threshold detector 217 may be adjusted differently than for ventricular sense amplifier 220 and threshold detector 227. As known to those skilled in this art, different settings may be necessary to account for differences in the physiology of the atria as compared to the ventricles.

Figure 5:
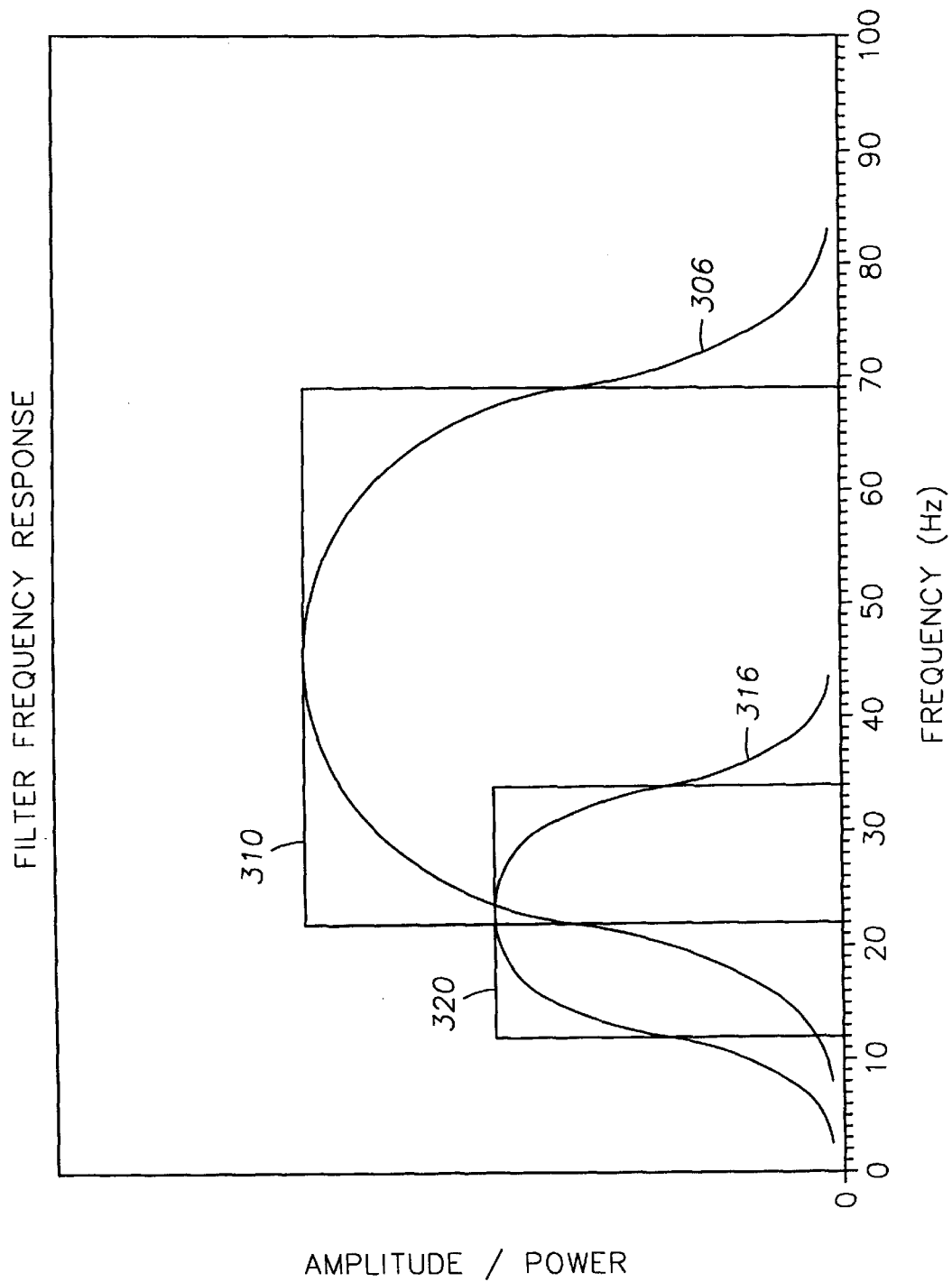
FIG. 5 is a frequency plot showing a typical spectrum of an exemplary atrial electrogram with both normal sinus rhythm and atrial fibrillation and the frequency response of the dynamically adjustable band pass filter of FIG. 4 according to the present invention.

DABPF 215 preferably is a band pass filter whose frequency response is dynamically adjusted when logic and control unit 250 switches pacing modes. For example, pacer 100 may operate in the DDD mode during normal sinus rhythm, but switch to the VVIR mode generally when normal sinus rhythm ceases, as indicated at time 55 in FIG. 3. To best understand the operation and function of DABPF 215, reference is now made to FIG. 5 which shows exemplary frequency spectrums of the atrial electrogram during normal sinus rhythm (spectrum 306) and during atrial fibrillation (spectrum 316). During NSR, most of the frequency content of the AEGM lies within the range of 20 to 70 Hz, with peak power at approximately 45 to 55 Hz, as shown by spectrum 306. During atrial fibrillation, however, the frequency spectrum of the AEGM shifts substantially to lower frequencies and includes signals of lower power, as shown by frequency spectrum 316. The reduction in power results from the reduction in AEGM amplitude during atrial fibrillation (FIG. 3). Most of the frequency content of atrial fibrillation is in the range of 10 to 40 Hz with peak power at approximately 20 to 25 Hz. The AEGM frequency spectrums of NSR and AF shown in FIG. 5 are exemplary and vary from patient to patient. As will be seen below, pacer 100 can be uniquely calibrated to enhance the sensitivity of DABPF 215 to the AEGM of the patient in which pacer 100 is implanted to provide increased ability to detect atrial fibrillation.

Band pass filters of conventional pacemakers generally include a frequency response similar to frequency response 310. The pass band of such filters pass signals whose frequency lies generally within the band of 22 to 69 Hz, although the precise delineation of the pass band varies from pacemaker to pacemaker. Although generally adequate for NSR, such filters often fail to adequately detect atrial fibrillation which has considerable frequency content in the lower stop band of the filter (0–22 Hz).

The DABPF 215 of the present invention enhances detection of atrial fibrillation by allowing the pass band of the filter to be adjusted dynamically. Referring now to FIGS. 4 and 5, to enhance the sensitivity of pacer 100 to the atrial electrogram during atrial fibrillation, the frequency response of the DABPF 217 is altered from the frequency response 310 to response 320. Frequency response 320 preferably includes a pass band with a lower limit of approximately 11 Hz and an upper limit of approximately 34 Hz.

As stated previously, DABPF 215, as well as band pass filter 225, may comprise a switched capacitor filter. As those of ordinary skill in the art will recognize, the frequency response of a switched capacitor filter is determined by the frequency of one or more clock signals provided to the filter. Thus, by changing the frequency of the clock signal to the filter, the filter's frequency response can be altered. A control signal on line 255 is provided from logic and control unit 250 to DABPF 215 to alter the frequency response of the filter. The control signal represents a clock signal whose frequency is adjustable by logic and control unit 250. For other types of filters used to implement DABPF 215, the signal on line 255 includes any signal necessary to change the frequency response of the DABPF 215, as would be known by those of ordinary skill in the art.

Broadly, according to known pacemaker methodology, logical and control unit 250 monitors the output signals from atrial and ventricular threshold detectors 217, 227 to determine if the patient is experiencing NSR. This determination generally is made by computing or measuring the time between the output pulses from the threshold detectors that are produced in response to sensed atrial or ventricular activity. In this manner, pacer 100 can determine the rate of naturally occurring atrial and ventricular contractions and thus can estimate heart rate. During NSR, pacer 100 preferably operates in the DDD mode, as described previously. However, pacer 100 may determine that the patient is no longer experiencing NSR because the atria, for example, may be naturally contracting at an excessively slow or high rate which may be an indication of atrial fibrillation, asystole, vasovagal syncopy, or other atrial arrhythmias. During periods of bradycardia the pacer paces the atrium at the programmed lower rate limit (DDD mode) or the sensor indicated rate (DDDR mode). During such conditions, pacer 100 preferably mode switches to VVIR mode and generally paces at a rate determined by activity sensor 260. In addition to the mode switch, logic and control unit 250 also initiates a change in the frequency response of DABPF 215 to frequency response 320 (FIG. 5) to enhance detection and monitoring of the AEGM during the VVIR mode. Frequency response 320 is adapted for increasing the sensitivity of pacer 100 to lower frequencies. AF typically is characterized by lower frequency signals and thus pacer 100 increases its sensitivity to AF and can then more likely distinguish AF from other atrial arrhythmias.

Figure 1:
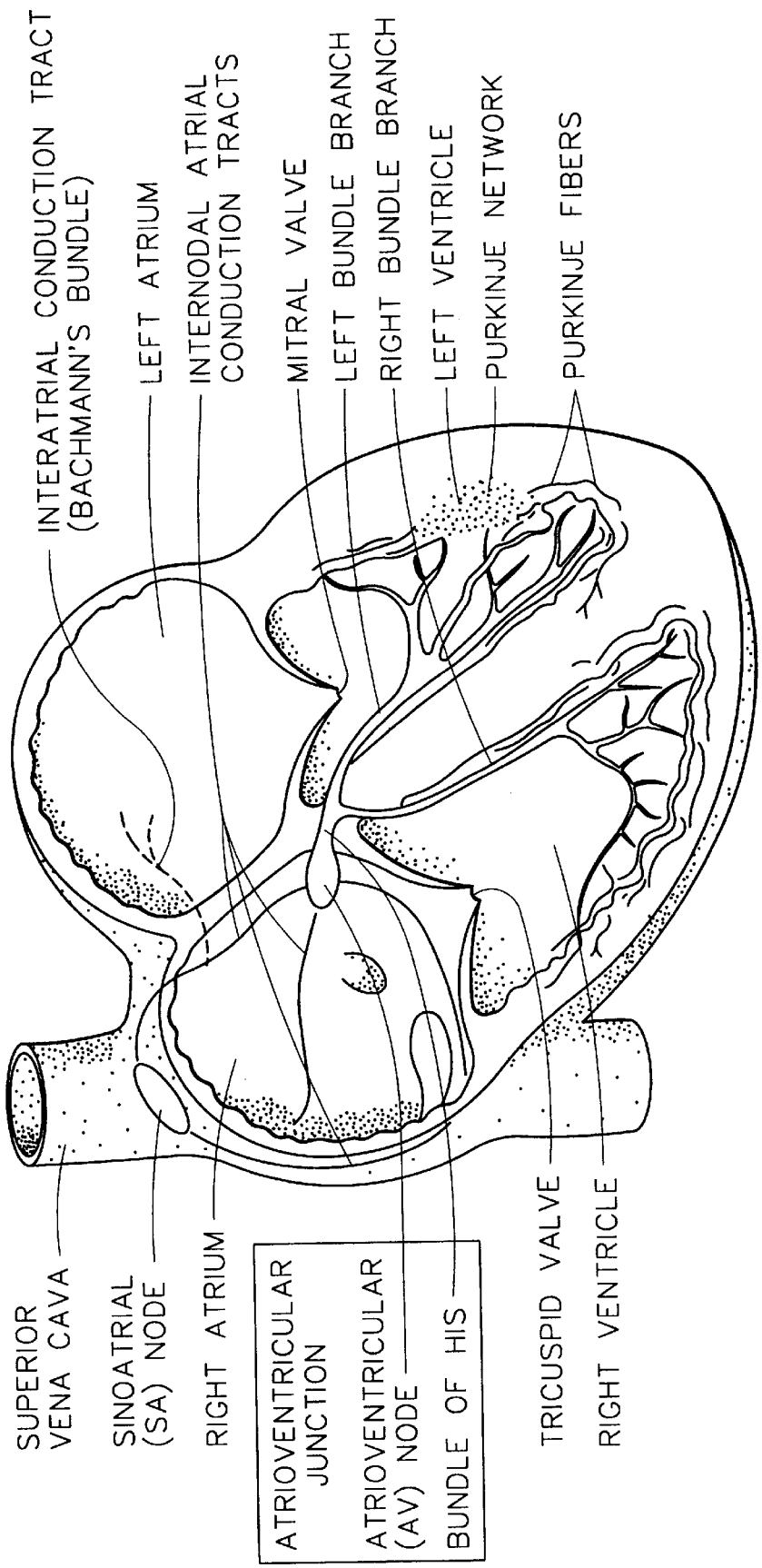
FIG. 1 is a schematic cut-away view of a human heart, in which the various relevant parts are labeled.
Figure 2:
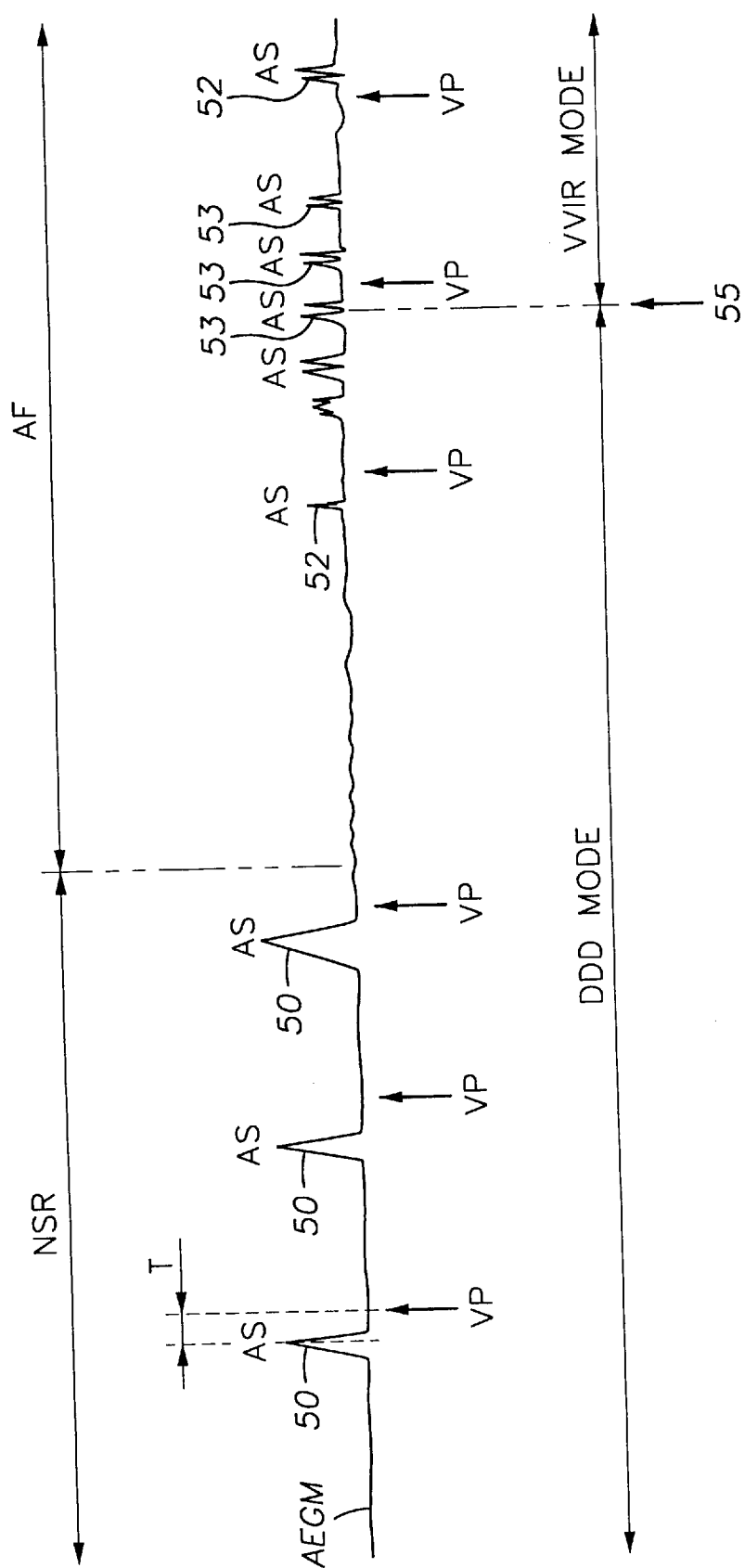
FIG. 2 shows an exemplary atrial electrogram during normal sinus rhythm and during atrial fibrillation.
Figure 6:
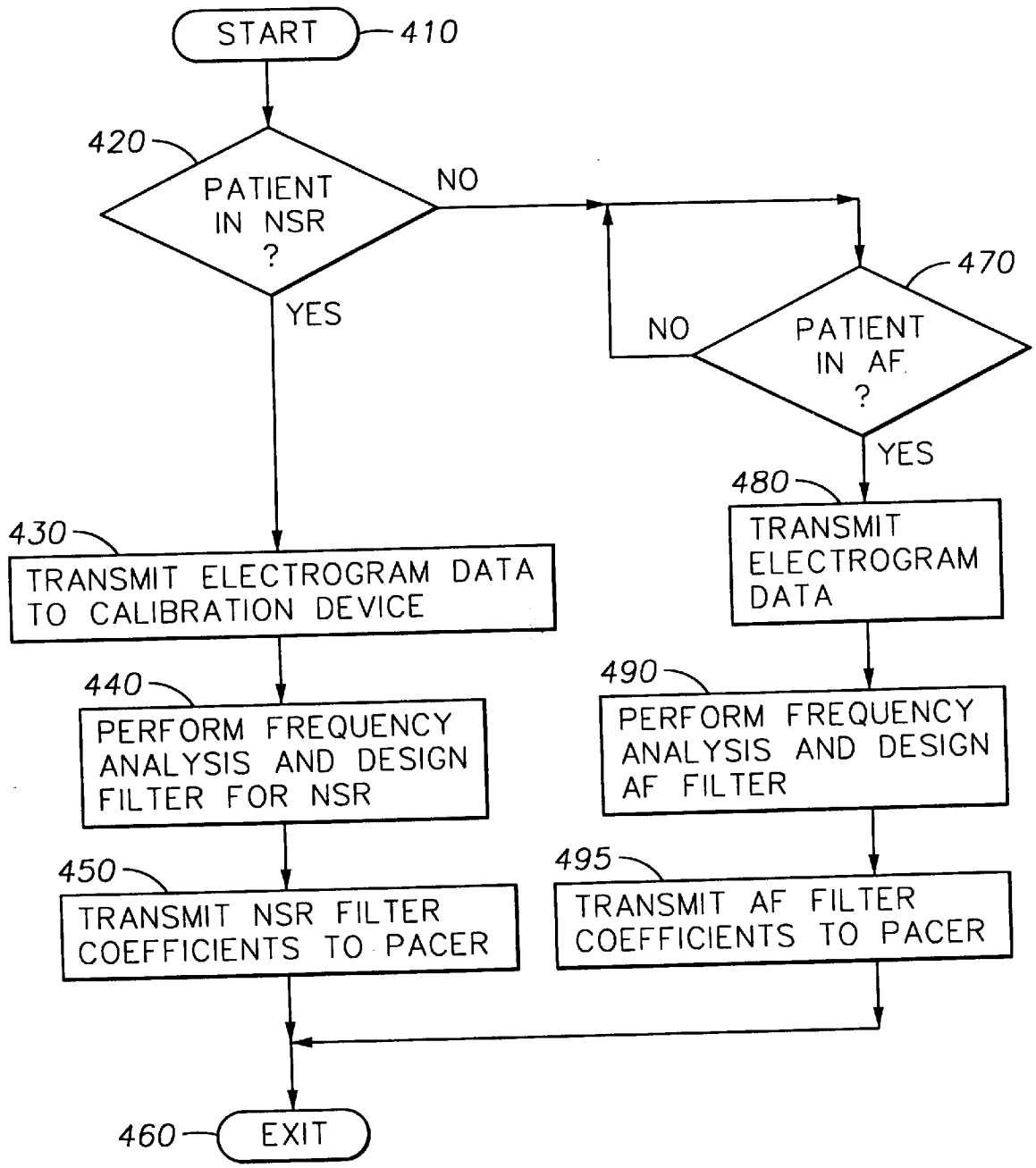
FIG. 6 is a flow chart representing the steps for tailoring the frequency response of the dynamically adjustable band pass filter of FIG. 4.
Figure 7:
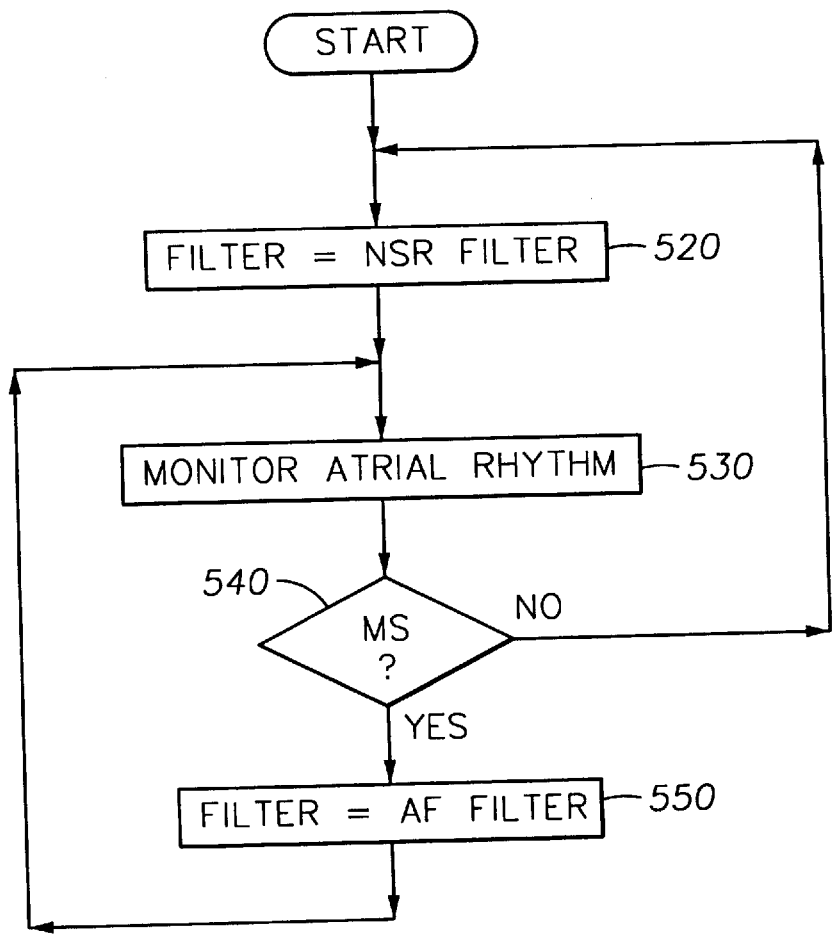
FIG. 7 is a flow chart representing the steps for controlling the frequency response of the dynamically adjustable band pass filter of FIG. 4 upon detection of a condition for switching the mode of operation of the pacer.

The operation and calibration of pacer 100 will now be described with reference to FIGS. 4–7. FIG. 6 is a flow diagram for tailoring the frequency response of DABPF 215 (FIG. 4) using external programmer 400 (FIG. 2). FIG. 7 is a flow diagram for dynamically changing the frequency response of DABPF 215 upon a mode switch as described previously.

NSR filter response 310 and AF filter response 320 (FIG. 5) may vary from patient to patient and will be set based upon the frequency spectrum of each patient's NSR and AF atrial electrogram. The tailoring routine thus determines a suitable frequency response for the DABPF 215 during both normal sinus rhythm and atrial fibrillation. During the tailoring operation, atrial electrogram data is transmitted from the implanted pacer 100 to the programmer 400 located external to the body as shown in FIG. 3. The programmer 400 preferably includes a computer or any other device capable of receiving and analyzing data to design an appropriate filter for processing and enhancing the data. Tailoring preferably is performed during the implantation procedure or during a post operative visit to the physician's office. Telemetry unit 270 preferably allows two-way communication along a communication path 405 between the implantable medical device 100 and the external programmer 400 as is known by one of ordinary skill in the art and described above.

As explained below, calibration requires obtaining a sample of an atrial electrogram from the patient during normal sinus rhythm and during atrial fibrillation. NSR data is usually easily obtained because the patient normally experiences NSR and is likely to be experiencing NSR at the time tailoring is performed. Obtaining AF data, however, is problematic because a patient typically experiences AF relatively infrequently and even then at unpredictable times. Thus, it is quite likely that the patient's heart will not be experiencing AF naturally (i.e., without artificial stimulation) while tailoring is performed. Two techniques for inducing AF, however, are possible.

The first technique involves inducing atrial fibrillation by rapid atrial pacing. Normally, atrial fibrillation can be induced by providing 10 electrical pulses to the atrial electrode in a one second period of time, although faster rates such as 60 Hz also are suitable for inducing atrial fibrillation.

The second technique requires storing a sample of naturally occurring atrial fibrillation data in the pacer's RAM memory. During those unpredictable times that the patient experiences atrial fibrillation, the pacer 100 detects, samples, and stores a sufficient quantity of AEGM to use for subsequent tailoring. The sampling rate may be 250 samples/second. Five seconds worth of atrial electrogram including atrial fibrillation is usually enough for proper tailoring. Although the quality of the AEGM waveform stored in the pacer's RAM during atrial fibrillation may suffer because DABPF 215 may not be tailored, the waveform generally will be sufficient to determine the appropriate frequency response for DABPF 215. Preferably, however, sampling occurs without band pass filtering the electrogram at all.

Referring now to FIG. 6, the tailoring routine begins at step 410. External programmer 400 preferably initiates tailoring by transmitting a start tailoring signal to pacer 100 over transmission path 405 (FIG. 3). In step 420, if pacer 100 determines that the patient is experiencing normal sinus rhythm, then a 10 to 15 second sample of the atrial electrogram is sampled, digitized and transmitted to the external programmer 400 in step 430. In step 440, programmer 400 performs a frequency analysis on the NSR data and designs a band pass filter with a band pass to match the frequency content of the NSR data. Techniques for performing the frequency analysis, including fast fourier transforms, and designing the appropriate filter are readily known by those of ordinary skill in the art and thus are not provided explicitly herein for sake of simplicity. Generally, however, it is known that filters can be characterized by a set of coefficients corresponding to the coefficients of the terms of the denominator polynomial in the filter's transfer function. See e.g. M. S. Ghausi and K. R. Laker, *Modern Filter Design*. N.J. Prentice-Hall, 1981. Those of ordinary skill in the art will recognize that any filter can be mathematically characterized by its coefficients and that the coefficients dictate the values of the components, namely resistors and capacitors, comprising the filter. Finally, in step 450 the filter coefficients are transmitted back to pacer 100 and preferably are stored in the pacer's memory for subsequent use by DABPF 215.

Before or after steps 430–450 are performed to determine the appropriate filter for the patient's NSR atrial electrogram, steps 470, 480, 490, and 495 are performed to design a filter for pacer 100 to enhance the atrial electrogram during atrial fibrillation. Atrial fibrillation may be induced using either of the methods described above. If the patient, in fact, is experiencing atrial fibrillation during the tailoring procedure (either naturally or induced by rapid atrial pacing), the result of decision step 420 will be "no" and the result of decision step 470 will be "yes" indicating the presence of atrial fibrillation. If the patient is neither in NSR nor AF, the result of decision steps 420 and 470 will be "no" and control loops at decision step 470 until AF is induced according to the previously discussed technique. Consequently, in step 480 preferably 4 to 6 seconds of the patient's atrial electrogram is sampled, digitized, and transmitted to external programmer 400 for analysis. The AEGM at this point includes atrial fibrillation. In step 490, programmer 400 performs a frequency analysis on the data and designs a filter with a frequency response corresponding to the frequency spectrum of the sampled AEGM. Finally, in step 495 the appropriate filter coefficients are transmitted back to pacer 100 and preferably stored for subsequent use by DABPF 215. After the appropriate NSR and AF filter frequency responses have been designed and the appropriate filter coefficients have been downloaded to pacer 100, calibration ends at step 460.

If atrial fibrillation is not induced during calibration, and instead a previously stored AF electrogram waveform is transmitted to programmer 400, a code may be included in the electrogram data to distinguish NSR data from AF data. Thus, decision step 420 may be replaced with a decision to check the code to determine if the transmitted waveform is AF or NSR data. If the waveform represents NSR data, steps 430–450 are performed, and if the waveform represents AF data, steps 480–495 are performed. Decision step 470 is unnecessary where coded waveforms are transmitted.

Referring now to FIG. 7, the operation of pacer 100 to provide dynamic bandwidth control to enhance the pacer's sensitivity to atrial fibrillation is shown. Normally, DABPF 215 is set to provide the frequency response for normal sinus rhythm (step 520). The filter coefficients determined during calibration and corresponding to NSR are used to determine and appropriate clock frequency for the control signal on line 255 (FIG. 4) to DABPF 215. Selecting the appropriate clock frequency of course assumes DABPF 215 is a switched capacitor filter. For other filter topologies, the control signal on line 255 will be an appropriate signal to adjust the frequency response of DABPF 215 to a response dictated by the filter coefficients, as those of ordinary skill in the art will understand.

The pacer 100 monitors the atrial electrogram in step 530. If no mode switch is needed in step 540 (e.g., the heart remains in NSR), control loops back to step 520 ensuring that the NSR frequency response is maintained. The term "mode switch" in decision step 540 refers to whether the pacer is in the preferred mode during NSR, such as DDD mode, or in an alternative mode, such as VVIR mode upon detection of AF. Thus, a "no" answer in decision step 540 means the pacer should go into the preferred NSR mode, or remain in that mode if already in that mode. A "yes" answer means the pacer should go into the alternative mode, or remain there if currently in the alternative mode.

Thus, if the pacer determines that a condition such as atrial fibrillation warrants a transition into mode switch in step 540, logic and control unit 250 directs DABPF 215 to change its frequency response in step 550 to the appropriate atrial fibrillation response determined during calibration (FIG. 6). Control then loops back to step 530 in which the atrial electrogram is again monitored. Once AF ceases and no mode switch is needed in step 540, the frequency response of DABPF 215 is reset to the NSR response in step 520.

While preferred embodiments of this invention have been shown and described, modifications thereof can be made by one skilled in the art without departing from the spirit or teaching of this invention. The embodiments described herein are exemplary only and are not limiting. Many variations and modifications of the system and apparatus are possible and are within the scope of the invention. Accordingly, the scope of protection is not limited to the embodiments described herein, but is only limited by the claims which follow, the scope of which shall include all equivalents of the subject matter of the claims.

What is claimed is:

1. A medical device for electrically stimulating the heart, comprising:

a logic and control unit for initiating a pacing pulse to be delivered to the heart;

an output multiplier/regulator coupled to said logic and control unit, said output multiplier/regulator receiving said pacing pulse from said logic and control unit and altering the magnitude of the pacing pulse;

a plurality of electrodes for coupling to the heart, said pacing pulse delivered to the heart through said electrodes; and a sense circuit including a band pass filter which includes a dynamically adjustable frequency response, said frequency response is dynamically adjustable by an external device, said sense circuit providing to said logic and control unit an electrical signal indicative of electrical activity in a predetermined chamber of the heart;

said logic and control unit provides different modes of pacing and switches modes depending upon predetermined conditions, and wherein said dynamically adjustable frequency response of said band pass filter is adjusted upon a mode switch.

2. The medical device of claim 1 wherein said logic and control unit provides different modes of pacing and switches modes depending upon predetermined conditions, and wherein said dynamically adjustable frequency response of said band pass filter is adjusted in response to a control signal from said logic and control unit.

3. The medical device of claim 1 wherein said frequency response of said dynamically adjustable band pass filter is adjusted upon a mode switch to increase said medical device's sensitivity to atrial fibrillation.

4. The medical device of claim 1 wherein said medical device includes memory for storing filter coefficients for determining the frequency response of said dynamically adjustable band pass filter.

5. The medical device of claim 1 wherein said dynamically adjustable band pass filter comprises a switched capacitor filter.

6. The medical device of claim 5 wherein said control signal from said logic and control unit is a clock signal.

7. The medical device of claim 6 wherein said dynamically adjusted frequency response is determined by said clock signal.

8. The medical device of claim 7 wherein said dynamically adjusted frequency response is adjusted by changing the frequency of said clock signal.

9. The medical device of claim 8 wherein said logic and control unit adjusts the frequency response of said band pass filter by adjusting the frequency of said clock signal.

10. A method for calibrating an implantable pacemaker having a dynamically adjustable band pass filter, said method using an external calibration device and comprising the steps of:

(a) transmitting an electrogram waveform to said calibration device;

(b) performing a frequency analysis on said electrogram waveform with said calibration device;

(c) determining a frequency response suitably sensitive to said electrogram;

(d) determining filter coefficients for implementing said frequency response; and (e) transmitting said filter coefficients from said calibration device to said implantable pacemaker.

11. The method of claim 10 wherein said transmitted electrogram in step (a) includes normal sinus rhythm.

12. The method of claim 10 wherein said transmitted electrogram in step (a) includes atrial fibrillation.

13. The method of claim 10 further including the steps of inducing atrial fibrillation and obtaining an electrogram including said atrial fibrillation before performing step (a).

14. A method for calibrating an implantable pacemaker having a dynamically adjustable band pass filter said method using an external calibration device and comprising the steps of:
   (a) detecting atrial fibrillation;
   (b) storing a sample of an atrial electrogram including said detected atrial fibrillation in a memory device in said pacemaker;
   (c) determining a first frequency response and a second frequency response for said dynamically adjustable band pass filter wherein said first frequency response is suitably sensitive for normal sinus rhythm and said second frequency response is suitably sensitive for atrial fibrillation.

15. The method of claim 14 wherein said step of determining a first and a second frequency response (step c) includes the steps of:
   (c)(1) transmitting a first electrogram waveform to said calibration device, said first electrogram including normal sinus rhythm;
   (c)(2) transmitting a second electrogram waveform to said calibration device, said second electrogram including atrial fibrillation; and
   (c)(3) performing a frequency analysis on said first and said second electrograms.

16. The method of claim 15 further including the step of:
   (c)(4) determining said first frequency response suitably sensitive to said first electrogram;
   (c)(5) determining a first set of filter coefficients for providing said first frequency response;
   (c)(6) determining said second frequency response suitably sensitive to said second electrogram;
   (c)(7) determining a second set of filter coefficients for providing said second frequency response; and
   (c)(8) transmitting said first and said second sets of filter coefficients from said calibration device to said implantable pacemaker.

17. A method for electrically stimulating a heart using an implantable pacemaker that includes a pacing circuit, a sense circuit including a dynamically adjustable band pass filter, and a logic and control unit, comprising the steps of:
   (a) operating said pacemaker in a first pacing mode with said band pass filter set to a first frequency response;
   (b) monitoring an electrogram;
   (c) switching said pacemaker to a second pacing mode upon detection of a first event in the electrogram; and
   (d) increasing the sensitivity of the sense circuit to said electrogram upon mode switching.

18. The method of claim 17 further including the steps of:
   (e) switching said pacemaker to said first pacing mode upon detection of a second event in said electrogram; and
   (f) changing the frequency response of said band pass filter to said first frequency response.

19. The method of claim 18 wherein said first event includes atrial fibrillation.

20. The method of claim 19 wherein said second event includes normal sinus rhythm.

21. The method of claim 17 wherein step (d) comprises the step of setting said band pass filter to a second frequency response that is lower than said first frequency response.

22. A medical system for monitoring the heart, comprising:
   an implantable medical device including a processor coupling together an atrial sense circuit having a dynamically adjustable band pass filter and a telemetry unit; and
   an external calibration device adapted to communicate to the implantable medical device;
   wherein said telemetry unit transmits atrial electrogram data to said calibration device; and wherein said calibration device determines a set of filter coefficients for dynamically adjusting said dynamically adjustable band pass filter to provide a frequency response that increases the medical device's sensitivity to said transmitted atrial electrogram data.

23. The medical system of claim 22 wherein said set of filter coefficients is transmitted to said medical device through said telemetry unit.

24. The medical system of claim 23 wherein said medical device includes memory for storing said filter coefficients.

* * * * *